(12) United States Patent
Hsu et al.

(10) Patent No.: US 6,245,939 B1
(45) Date of Patent: Jun. 12, 2001

(54) PROCESS FOR PRODUCING HIGHLY PURE AROMATIC CARBOXYLIC ACIDS

(75) Inventors: Yu-Wei Hsu, Chung Li; Chen-Long Lin, Hsin Chuang, both of (TW)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/201,634

(22) Filed: Nov. 30, 1998

(51) Int. Cl.$^7$ ..................................................... C07C 51/42
(52) U.S. Cl. ............................ 562/485; 562/486; 562/487
(58) Field of Search ............................... 560/78; 562/485, 562/486, 487

(56) References Cited

U.S. PATENT DOCUMENTS

| | | | | |
|---|---|---|---|---|
| 4,626,598 | * | 12/1986 | Packer et al. | 562/487 |
| 4,629,715 | * | 12/1986 | Schroeder | 502/185 |
| 5,062,709 | * | 11/1991 | Slee | 356/335 |

* cited by examiner

Primary Examiner—Samuel Barts
(74) Attorney, Agent, or Firm—Charles E. Krukiel

(57) ABSTRACT

An improved process for producing highly pure aromatic carboxylic acid from an impure solid acid product whereby the solid acid product is efficiently dissolved in a suitable solvent at relatively low temperatures despite the presence of solid lumps.

4 Claims, 1 Drawing Sheet

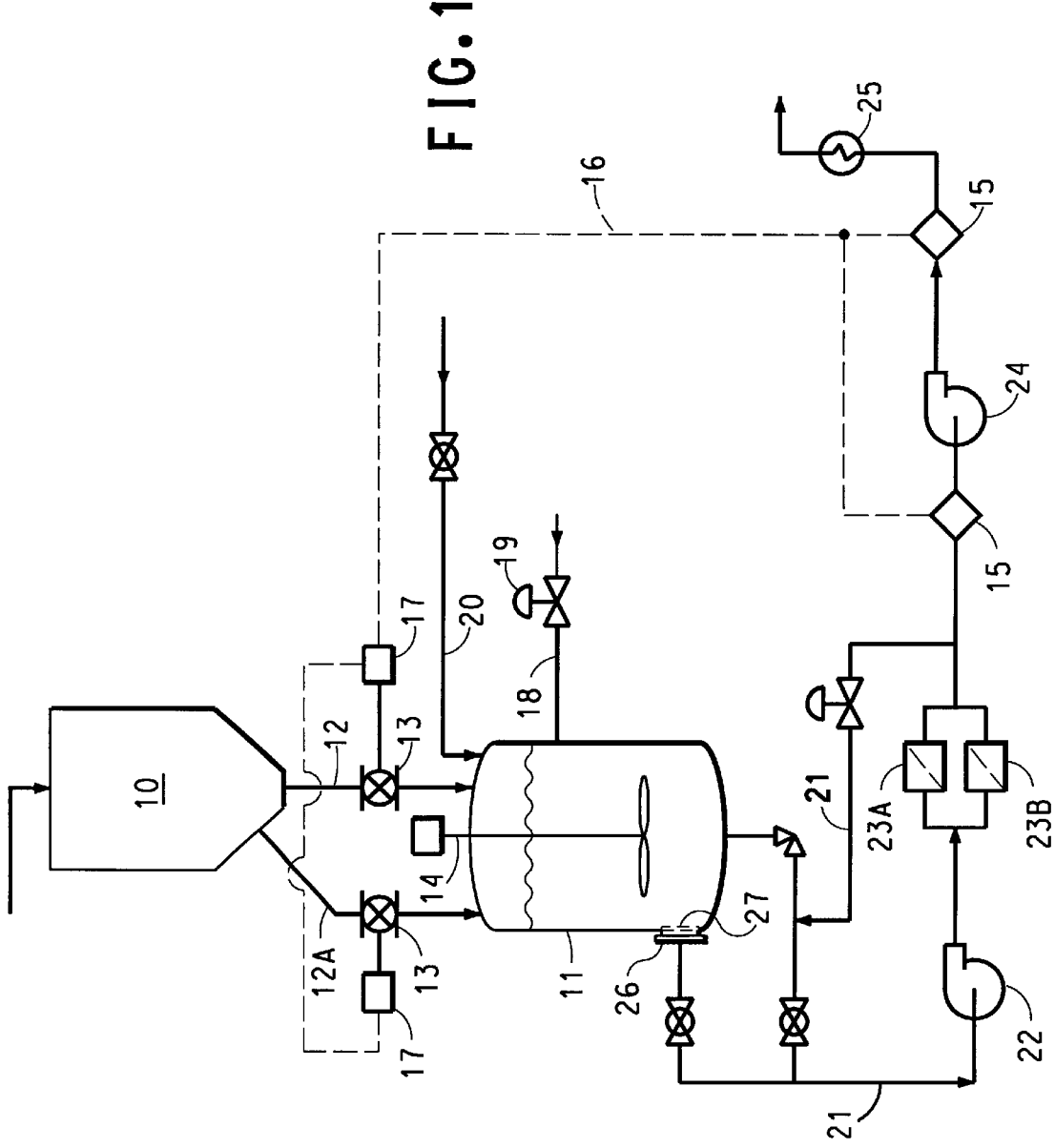

PROCESS FOR PRODUCING HIGHLY PURE AROMATIC CARBOXYLIC ACIDS

BACKGROUND OF THE INVENTION

The present invention relates to an improved process for producing highly pure aromatic carboxylic acid from an impure solid acid product, and, more particularly, to a process improvement whereby the solid acid product can be efficiently dissolved in a suitable solvent at relatively low temperatures despite the presence of solid lumps.

In typical commercial processes for producing highly pure aromatic carboxylic acids, and particularly isophthalic and terephthalic acid, a rather insoluble, impure acid is first produced and recovered from an oxidation process. In the oxidation process, which involves catalytic air oxidation of paraxylene in acetic acid solvent in the case of terephthalic acid, the impure acid, usually in the form of solid crystals, is conveyed from a dryer to a holding silo before further processing in a usually separate purification stage to remove impurities. In the purification stage of such a process, crude, i.e., impure, acid crystals are slurried in water, recycled mother liquor or other suitable solvent, and the resulting slurry is pumped through a series of preheaters to raise the slurry temperature and thereby dissolve the slurry particles. The resulting solution is then subjected to hydrogenation at elevated temperature typically in the range of 280°–283° C. under liquid phase conditions in the presence of a Group VIII noble metal hydrogenation catalyst. The purified acid is recovered by crystallizing the acid from the hydrogen treated solution. The principal impurities, which are p-toluic acid (m.p. 180° C.; b.p. 275° C.) derived from the compound 4-carboxybenzaldehyde (4-CBA) (m.p. 258° C.; b.p. sublimes) and unidentified color bodies, along with some other organic components, such as benzoic acid (m.p. 122.5° C.; b.p. 249° C.) and some residual terephthalic acid, (in the case of terephthalic acid) remain dissolved in the solution.

Depending on the conditions under which the crude acid is dried, its moisture content, and the time during which the acid is held in the holding silo before entering the purification stage, significant lumping of the solid product can occur. These lumps can be as large as 10 cm in average diameter, and, in turn, they can be very difficult to process, can clog and even damage valves and conveying equipment, and can be very difficult to efficiently dissolve in water and other solvents, especially at relatively low initial temperatures, i.e., below about 100° C., for further processing. The present invention provides a method for handling these lumps in the context of a process for producing highly pure aromatic carboxylic acid from a crude crystalline starting material.

SUMMARY OF THE INVENTION

The present invention is an improvement in a process for producing a highly pure aromatic carboxylic acid crystals from an impure solid acid product which includes the steps of:
  (a) dissolving the impure solid product in a solvent at elevated temperature to form a solution;
  (b) hydrogenating the solution in the presence of a hydrogenation catalyst;
  (c) optionally separating the solution from the catalyst; and
  (d) cooling the solution to precipitate pure aromatic carboxylic acid crystals. The improvement comprises dissolving the impure solid product in the solvent by metering the impure solid product from its storage silo through an appropriate exit nozzle into a holding tank containing the solvent in response to a feedback signal. It is thereby possible to form an intermediate slurry of impure acid crystals at a relatively low temperature in the range of from 90° C. to 100° C. and at a concentration in a range of from 28% w/w up to 30% w/w while continuously agitating the slurry as it is formed. The slurry is then removed, i.e., pumped, from the holding tank while undesirably large lumps of yet undissolved solid product, i.e., particles having an average size greater than from 24 mm to 28mm, are retained in the holding tank. The density of the slurry is continuously measured at a location downstream from the holding tank, and that measurement is then converted into a feedback signal which is communicated to the metering device to control the rate at which solid impure product and solvent are introduced into the holding tank. Simultaneously as the slurry is being pumped from the holding tank or thereafter via one or via several intermediate steps, the slurry is heated to an appropriately high processing temperature of about 283° C. and the pressure of the slurry is raised to an appropriate level at which substantially all of the acid particles have dissolved prior to hydrogenation and purification.

The process of the present invention can be operated on a continuous basis or batch-wise, and, in a preferred embodiment of the invention, metering of the solid impure product from its storage silo into the slurry holding tank is accomplished using a motor-actuated rotary valve having a control device which is responsive to the feedback signal.

BRIEF DESCRIPTION OF THE DRAWINGS

FIG. 1 is a simplified schematic diagram of a process improvement according to the invention.

DETAILED DESCRIPTION

The present invention is particularly applicable to a process for producing highly pure aromatic carboxylic acid crystals from a crude solid acid product. The aromatic carboxylic acids which are of most commercial interest are isophthalic acid and terephthalic acid, although the process is applicable for handling any impure solid acid product which undergoes a similar hydrogenation purification in solution.

A typical purification process to which the invention applies includes the steps of:
  (a) dissolving the impure solid product in a solvent at elevated temperature to form a solution;
  (b) hydrogenating the solution in the presence of a hydrogenation catalyst;
  (c) optionally separating the solution from the catalyst; and
  (d) cooling the solution to precipitate pure aromatic carboxylic acid crystals. In the case of isophthalic acid and terephthalic acid, water, which may include recycled aqueous mother liquor, is the preferred solvent, and it will be referred to in the discussion which follows to illustrate the invention.

The improvement according to the invention comprises dissolving the impure solid product in the solvent, e.g., water, by:
  (e) metering the impure solid product into a holding tank containing said solvent using a motor actuated metering device in response to a feedback signal to thereby form a slurry of impure acid crystals at a relatively low temperature in the range of from 90° C. to 100° C. and having a concentration in the range of from 28% w/w to 30% w/w while continuously agitating the slurry as it is formed;

(f) removing the slurry from the holding tank through a retaining screen whereby those particles of yet undissolved solid product which have a particle size greater than the openings in the screen are retained in the holding tank;

(g) measuring the density of the slurry downstream from the holding tank and converting the density measurement to a feedback signal;

(h) communicating the feedback signal to the metering device in step (e); and simultaneously therewith or thereafter (i) heating the slurry.

In practice on a commercial scale, a crude isophthalic or terephthalic acid is recovered from an oxidation process as a crystalline powder and conveyed to a storage silo to await further processing. The storage silo and related processing equipment, tanks, etc. and piping utilized in the purification process which follows are typically fabricated from a stainless steel or other alloy that can resist corrosion and avoid contamination of the reactants. The solid crystalline powder, in addition to chemical impurities formed during the oxidation reaction, may also contain residual solvent from earlier processing and washing, and it may have some concentration of moisture, all of which can contribute to a tendency for the crystal particles to cling together and form massive, hard lumps over time.

Purifying the crude, i.e., impure, acid product requires first dissolving the crystalline product in a solvent, such as, for example, demineralized or recycled water (i.e., mother liquor), or a mixture of the two. The rate at which the acid crystals can dissolve can be influenced by numerous factors, such as, particle (lump) size, concentration, temperature, pressure and agitation. For ease of processing it has been found most convenient to first form an aqueous slurry of the crude acid at a relatively low temperature in the range of from 90° C. –100° C. in an intermediate "slurry holding tank" which is equipped with an agitator for continuously mixing the slurry as it forms and thereby enhancing the rate of dissolution.

Referring now to FIG. 1, crude acid crystals are metered from storage silo 10 into slurry holding tank 11 through a one of two possible discharge nozzles or lines. Illustrated in FIG. 1 is a primary discharge line 12 which comes directly off the conical base of the storage silo and secondary discharge line 12A which comes off the side of the conical section as shown. Each discharge line is equipped with a motor-actuated metering device, which, in a preferred embodiment of the invention, is a motor-actuated rotary valve 13 of suitable diameter, e.g. not less than about 20 cm in diameter. The speed of rotary valve 13 is controlled by a slurry density controller. The controller output is via an invertor to control the speed of the rotary valve drive motor in the range of from 0 to 22 rpm.

Storage silo 10 is typically located directly above slurry holding tank 11 as shown greatly simplified in the figure, and slurry holding tank 11 is equipped with an agitator 14 for continuously agitating the slurry as it is formed. A vertically positioned single impeller axial downflow agitator 14 is shown which typically operates at about 68 rpm. However, any suitable means of agitation may be used that can be installed for continuous operation.

Motor-actuated rotary valves 13 in lines 12 and 12A are arranged to meter impure acid product from storage silo 10 into slurry holding tank 11. Powder flow rate can be measured using a commercially available powder flow meter of the type which simultaneously measures density and velocity and then converts these measurements to mass flow rate. Slurry strength is then controllable by controlling the powder mass flow rate at a fixed ratio to the total solvent flow rate into slurry holding tank 11. In the embodiment shown in FIG. 1 an alternative control scheme is illustrated using slurry density measurement. A feedback signal is generated from one or both of density measuring devices 15 which are located as shown downstream of slurry holding tank 11. Slurry density is typically maintained at about 1085 kg/m$^3$. The density measurement has a direct relationship to the slurry strength, i.e., density, and is used to adjust the crude acid flow rate into slurry holding tank 11 according to pre-selected set points. The density measurement is converted to a feedback signal which is transmitted via dotted line 16 to either one of motor control devices 17, which, in turn, controls the rate at which the respective motor turns its corresponding rotary valve 13. In practice, only one of line 12 or 12A is used at a time in operating the process. Recycled water is introduced into slurry holding tank 11 via line 18 and control valve 19, and fresh water can be added to slurry hold tank 11 via line 20. In addition, solvent, typically cold demineralized water, can be introduced into slurry holding tank 11 via a flush water spray through the slurry holding tank vent line (not shown). The total flow of solvent into slurry holding tank 11 is controlled by a commercially available high- and low-level control means.

The purification stage is based on an overall process design whereby the aqueous slurry formed in slurry holding tank 11 is carefully controlled to maintain a solids strength in the range of 28% to 30% w/w based on a crude acid design flow rate of 55 tes/hr and a solvent design flow rate of 128.3 tes/hr. Slurry concentration can vary higher or lower, but usually such a variation will produce a corresponding economic penalty in overall process efficiency. The temperature in slurry holding tank 11 is maintained in the range of from 95° C. to 100° C., although this range is not critical, and the pressure is atmospheric.

To achieve the desired elevated level of temperature and pressure for hydrogenation, the aqueous slurry is pumped through a predetermined series of pre-heaters, i.e., heat exchangers. As shown greatly simplified in reference to FIG. 1, the slurry is pumped from slurry holding tank 11 via line 21 around a pressure control loop via a low pressure dissolver feed pump 22. The low pressure dissolver feed pump is a horizontal centrifugal pump of suitable capacity and discharge pressure. Pressure in the control loop is typically maintained at about 10 bar (1000 kPa). Two process-operable filters 23A & 23B are positioned in parallel on the discharge side of low pressure dissolver feed pump 22 to remove any debris which may have found its way into the system. Only one of filters 23A and 23B is in use at any time. Slurry flows through a condensate injection heater (not shown) on its way to the suction side of high pressure dissolver feed pump 24 and then on to a first preheater 25 which raises the temperature of the slurry to an intermediate value in the range of 150° C. In operation, a series of high pressure dissolver feed pumps 24 boost the slurry pressure from about 10 bar (1000 kPa) to 110 bar (11,000 kPa) and deliver the slurry to the purification reaction stage through a train of preheaters. These additional preheaters, arranged in series (not shown), raise the temperature of the slurry to the required operating temperature for the purification reaction, which is in the range of 283° C. High pressure dissolver feed pumps are typically single-stage vertically mounted high-speed centrifugal pumps.

Slurry is withdrawn from slurry holding tank 11 through nozzle 26 located in the side wall of the holding tank. Nozzle 26 is sized to accommodate process design flow rates. With this configuration, undesirably large lumps of yet undissolved solid particles of crude acid are retained in the holding tank by perforated screen 27 positioned either internally as shown or externally over the opening for nozzle 26 whereby solid particles having an average particle size greater than 24 mm, i.e., too large to pass through the openings in the screen, are retained in slurry hold tank 11 and prevented from entering the downstream portion of the process until they have been sufficiently dissolved to pass through the screen openings. Although the description refers to "screen" 27, any suitable retaining means, for example, expanded metal, drilled or punched metal sheet, for placement over the nozzle opening to temporarily retain undesirably large solid particles in the slurry holding tank can be used in practicing the invention.

The slurry strength in the feed to the preheaters determines the terephthalic acid/isophthalic acid strength in the hydrogenation reactor. The solution strength, therefore, is critical to successful operation of the reactor, and control of feed slurry strength is very important.

As many widely different embodiments of this invention may be made without departing from the spirit and scope thereof, it is to be understood that this invention is not limited to the specific embodiments thereof except as defined in the appended clams, and all changes which come within the meaning and range of equivalents are intended to be embraced therein.

What is claimed is:

1. In a process for producing highly pure aromatic carboxylic acid from an impure solid acid intermediate product which includes the steps of:
    (a) hydrogenating a solution of the impure product at elevated temperature and pressure in the presence of a hydrogenation catalyst;
    (b) optionally separating the solution from the catalyst; and
    (c) cooling the solution to precipitate pure aromatic carboxylic acid crystals; the improvement comprising the steps of:
    (d) metering the impure solid acid intermediate product into a holding tank containing said solvent in response to a feedback signal thereby forming a slurry of impure acid crystals at a temperature in the range of 95° C. to 100° C. and having a concentration in the range of 28% to 30% w/w while continuously agitating the slurry as it is formed;
    (e) removing the slurry from the holding tank through a retaining screen whereby solid particles of undissolved impure product which are too large to pass through said screen are retained in said holding tank;
    (f) measuring the density of the slurry downstream of the holding tank and converting the measurement to a feedback signal;
    (g) communicating the feedback signal to step (d); and simultaneously therewith or thereafter
    (h) heating the slurry to thereby further dissolve the slurry particles.

2. The process of claim 1 in which the impure solid product is metered into the holding tank by a motor actuated rotary valve.

3. The process of claim 2 in which slurry is removed from the holding tank through a nozzle located in the sidewall of the holding tank, said nozzle having a screen mounted thereover for retaining in the holding tank said particles of undissolved solid product too large to pass through said screen.

4. The process of claim 3 in which the highly pure carboxylic acid is terephthalic acid.

* * * * *